United States Patent

Lee et al.

Patent Number: 5,944,717
Date of Patent: Aug. 31, 1999

[54] MICROMACHINED ELECTRICAL CAUTERIZER

[75] Inventors: Abraham P. Lee, Walnut Creek; Peter A. Krulevitch, Pleasanton; M. Allen Northrup, Berkeley, all of Calif.

[73] Assignee: The Regents of the University of California, Oakland, Calif.

[21] Appl. No.: 08/854,342

[22] Filed: May 12, 1997

[51] Int. Cl.[6] .................................................. A61B 17/39
[52] U.S. Cl. .............................. 606/48; 606/50; 606/51; 600/547; 600/564; 600/565
[58] Field of Search ................................ 606/48, 50, 51; 600/564, 565, 547

[56] References Cited

U.S. PATENT DOCUMENTS

| | | | |
|---|---|---|---|
| 4,936,281 | 6/1990 | Stasz | 606/48 |
| 4,953,559 | 9/1990 | Salerno | 600/564 |
| 5,078,717 | 1/1992 | Parins et al. | 600/48 |
| 5,085,659 | 2/1992 | Rydell | 606/50 |
| 5,098,431 | 3/1992 | Rydell | 606/48 |
| 5,217,458 | 6/1993 | Parins | 606/48 |
| 5,454,809 | 10/1995 | Janssen | 606/50 |
| 5,603,711 | 2/1997 | Parins et al. | 600/564 |
| 5,626,578 | 5/1997 | Tihon | 606/50 |

*Primary Examiner*—Lee Cohen
*Attorney, Agent, or Firm*—L. E. Carnahan

[57] ABSTRACT

A micromachined electrical cauterizer. Microstructures are combined with microelectrodes for highly localized electro cauterization. Using boron etch stops and surface micromachining, microneedles with very smooth surfaces are made. Micromachining also allows for precision placement of electrodes by photolithography with micron sized gaps to allow for concentrated electric fields. A microcauterizer is fabricated by bulk etching silicon to form knife edges, then parallelly placed microelectrodes with gaps as small as 5 μm are patterned and aligned adjacent the knife edges to provide homeostasis while cutting tissue. While most of the microelectrode lines are electrically insulated from the atmosphere by depositing and patterning silicon dioxide on the electric feedthrough portions, a window is opened in the silicon dioxide to expose the parallel microelectrode portion. This helps reduce power loss and assist in focusing the power locally for more efficient and safer procedures.

22 Claims, 3 Drawing Sheets

MICROMACHINED ELECTRICAL CAUTERIZER

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to electro cauterization, particularly to a micromachined electrical cauterizer, and more particularly to a microfabricated cauterizer which can be used in conjunction with irrigation and suction, tissue sampling, and drug delivery operations utilizing a single microtool, as well as being utilized as a biosensor.

In open surgery and laparoscopic surgery, it is very important to achieve sufficient homeostasis. This not only prevents the patient from bleeding extensively but also allows the surgeon to better visualize the operation. Heomostasis can be achieved by either high frequency (HF) current, laser, or simply clipping. HF current is most commonly used to energetically induce a method of achieving heomostasis and is generally inexpensive and reliable. Furthermore, the more focused the HF current the less traumatic it is for the patient and which can be accomplished by closer placed bipolar electrodes. It is also intuitively true that the sharper the tool the less bleeding due to a small incision. One of the problems for laparoscopic surgery is the constant removal of tools. By miniaturizing and integrating multi-functional devices, systems can be built that require fewer tool exchanges which means shorter surgery duration.

With bulk silicon micromachining, one is able to generate microgrippers, such as described and claimed in copending U.S. application Ser. No. 08/446,146, filed May 22, 1995, entitled "Microfabricated Therapeutic Actuator Mechanisms", now U.S. Pat. No. 5,645,564 issued Jul. 8, 1997; and mircrobiopsy devices having sharp knife edges at the intersection of the crystalline planes of silicon by anisotropic etching, such as described and claimed in copending U.S. application Ser. No. 08/887,780, filed Jul. 3, 1997, entitled "Microbiopsy/Precision Cutting Devices". Furthermore, suction and/or irrigation is often necessary besides the pure dissecting of tissue and/or depositing of medicines.

The present invention at least partially overcomes the above-mentioned tool exchange problems, and by appropriate microfabrication enable the conjunction of several operational procedures into one tool, thus simplifying surgical procedures. By micromachining of silicon, now a well established technique, in conjunction with well established photolithographic and material deposition techniques, many of the necessary surgical functions or procedures mentioned above can be carried out utilizing a single tool. This invention provides such a tool by combining electrocauterizing with drug delivery, biosensors, and microactuation. For example microbiopsy can be carried out in conjunction with sampling of tissue beneath the surface followed by cauterization of the sample area and depositing of a drug or medication to eliminate infection or for other purposes. Also, the electrodes for cauterization can be used as sensing devices to probe the electrical resistance in contact and discriminate between tissue/clots and provide feedback to the operator. Thus, the present invention involves a micro-electrical cauterizing tool made by silicon micromachining techniques in conjunction with photolithography and material deposition techniques, which can be used along or in conjunction with micro-procedures.

SUMMARY OF THE INVENTION

It is an object of the present invention to provide a micromachined electrical cauterizer.

A further object of the invention is to provide a micro-instrument capable of electro cauterization in conjunction with any or all of suction, irrigation, biopsied tissue and deposition of drugs or the like.

Another object of the invention is to provide a micromachined electrical cauterizer which can be utilized as a biosensor to discriminate, for example, between tissues and clots.

Another object of the invention is to provide a microfabricated instrument by silicon micromachining, combined with photolithography and material deposition to form microelectrodes, as well as silicon etching to form knife edges on the instrument adjacent to the microelectrodes.

Another object of the invention is to provide a microinstrument which includes sharp edges for a biopsy, biopsied tissue retaining means, and electro cauterization means.

Other objects and advantages of the present invention will become apparent from the following description and accompanying drawings. Basically the invention involves a micromachined electrical cauterizer, which can be utilized alone or in conjunction with other micro procedures, such as sampling tissue, depositing of drugs and suction and/or irrigation. Further the electrodes used for cauterization may also be used as sensing devices to probe the electrical resistance in contact therewith to discriminate between tissues and clots, thus forming a biosensor. By this invention it is shown that by miniaturizing and integrating multi-functional devices, instruments can be built that require fewer tool exchanges which result in a shorter surgery duration. The present invention creates a potential for a new field of medical technology of performing laparoscopic surgery intravascularly, by providing an array of microtools that can be integrated on minimally-invasive therapeutic tools preventing the need to remove and replace single function devices while performing surgery. In addition, the tool of this invention can improve precision microsurgery by reducing cost and increasing efficiency.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
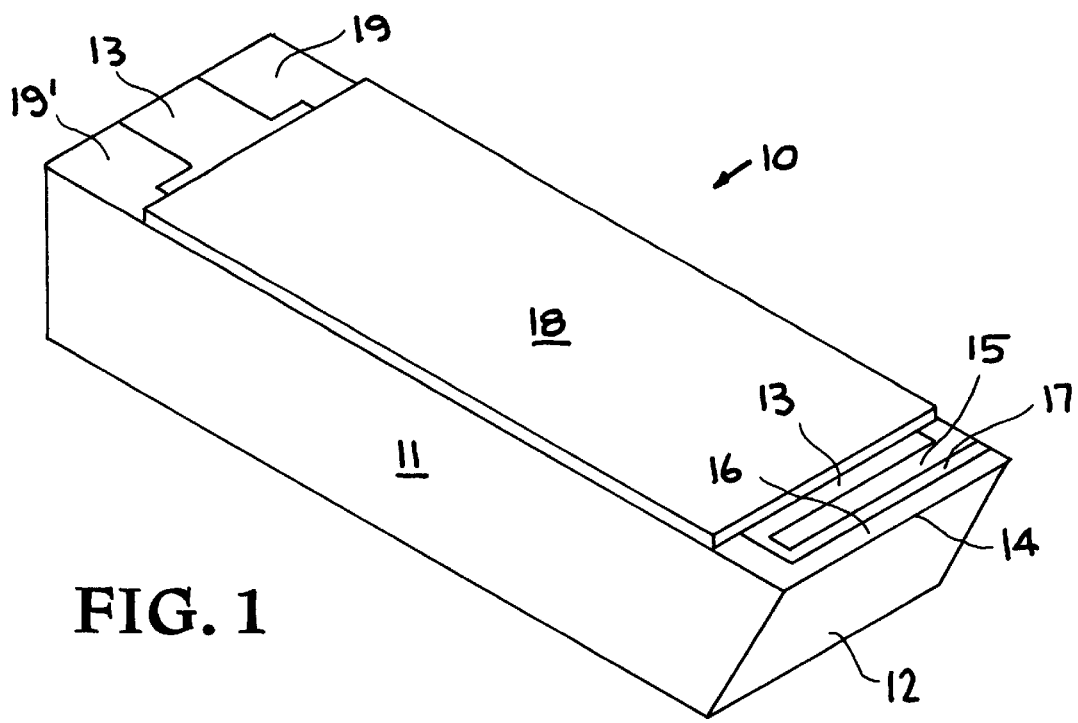
FIG. 1 is a perspective view of an embodiment of a silicon micromachined biopsy/electro cauterizer instrument made in accordance with the present invention.

The present invention is directed to a micromachined cauterizer utilizing silicon micromachining to combine a microstructure with microelectrodes for highly localized electro cauterization. The microfabricated cauterizer can be combined, for example, with means for obtaining tissue samples, means for irrigation and/or suction, and means for depositing drugs. In addition, the microelectrodes can be used for chemical sensing and neural probing/stimulation, such as tissue sensing of electrical resistance to discriminate between healthy tissue and clots/plaque. The microfabricated electrical cauterizer or instrument of this invention can be micromachined to carry out a number of operational procedures previously requiring individual instruments, as pointed out above.

The present invention is fabrication using the micro electromechanized systems (MEMS) technology and thus a surgeon may enter the treatment areas through the blood vessels (instead of transdermal incision holes) to perform intricate surgeries. This type of procedure enables a surgeon to reach treatment areas that are otherwise impossible to reach by existing therapies. Other possible applications include ex vivo tissue sampling and cell perforation and manipulation, such as electroporetic processes (i.e., DNA intake, etc.). There are also applications for this invention in genetic therapy since micromachined electrodes can generate large local electrical fields over a 10 $\mu$m input to patient. General application areas of using the cauterizer as a microelectrode include: 1) ablation treatment for arrhythmia, 2) treating vasospasm, 3) inducing drug uptake, 4) physiological stimulation and treatment. Thus instruments made in accordance with this invention can serve as a complete minimally-invasive diagnosis and treatment instruments for a variety of diseases.

The instrument of this may be fabricated using existing silicon micromachining techniques to provide a silicon microstructure with microelectrodes. Using boron etch stops and surface micromachining, microneedles with very smooth surfaces can also be made. Micromachining also allows for precision placement of electrodes by known photolithographic techniques with micron sized gaps to allow for concentrated electric fields. A first prototype microcauterizer, similar to the instrument of FIG. 1, was fabricated by bulk etching of the silicon body to form knife sharp edges. Parallel placed microelectrodes with gaps as small as 5 $\mu$m were patterned and aligned adjacent to the knife edges to provide homeostasis while cutting tissue. While most of the microelectrode lines were electrically insulated from the atmosphere by patterning and depositing an insulator, such as silicon dioxide, on the electrical feedthrough portions, a window was opened adjacent to the knife edge in the silicon dioxide to expose the parallel microelectrode portion. This helps to reduce power and assist in focusing the power locally for more efficient and safer procedures. Applications include minimally invasive intravascular therapies (including clot and plaque removal, tumor cell removal, microperforation for drug delivery), cataract eye surgery, open micro surgery, fine laparoscopic surgery, etc.

Referring now to the drawings, FIG. 1 illustrates an embodiment of a micromachined electrical cauterizer in conjunction with a single edge biopsy tool. The tool, generally indicated at 10, comprises a body or member 11, constructed of silicon, having a tapered end 12 which terminates at an upper surface 13 of the silicon body 11 in an etched knife edge 14 (formed by anisotropic etching which provides atomic sharpness). The body 11 may be also constructed of glass, ceramics, or metals. Parallel microelectrodes generally indicated at 15 and 16 are deposited on the surface 13 of silicon body 11 so as to define a cauterizing bipolar gap 17 adjacent knife edge 14, the electrodes being covered by an insulator layer or film 18, such as silicon dioxide, and are connected, as indicated by leads 19 and 19', to an electrical power supply via an attached catheter, not shown. Also, while not shown, the body 11 may include a hollow section to trap sample tissue. The parallel electrode arrangement is more clearly seen in FIG. 1A wherein the bipolar gap 17 is formed intermediate electrodes 15 and 16.

By way of example, the FIG. 1 tool 10 may be fabricated to have a length of 1 mm to 2 cm, width of 50 $\mu$m to 2 mm, height of 50 $\mu$m to 1 mm, with end 12 tapering at 15 to 55°, the insulation film 18 having a width of 50 $\mu$m to 2 mm and thickness of 0.5 $\mu$m to 3 $\mu$m, with the electrode bipolar gap 17 being 2 to 15 $\mu$m. The electrical energy supplied to the parallel electrodes 15 and 16 via leads 19 and 19' being, for example, 4 MHz/5V amp (60 W or $10^2$–$10^4$ W/cm$^2$) so as to generate heat in the range of 100° C. to 400° C., needed to cauterize the adjacent tissue.

Figure 1A:
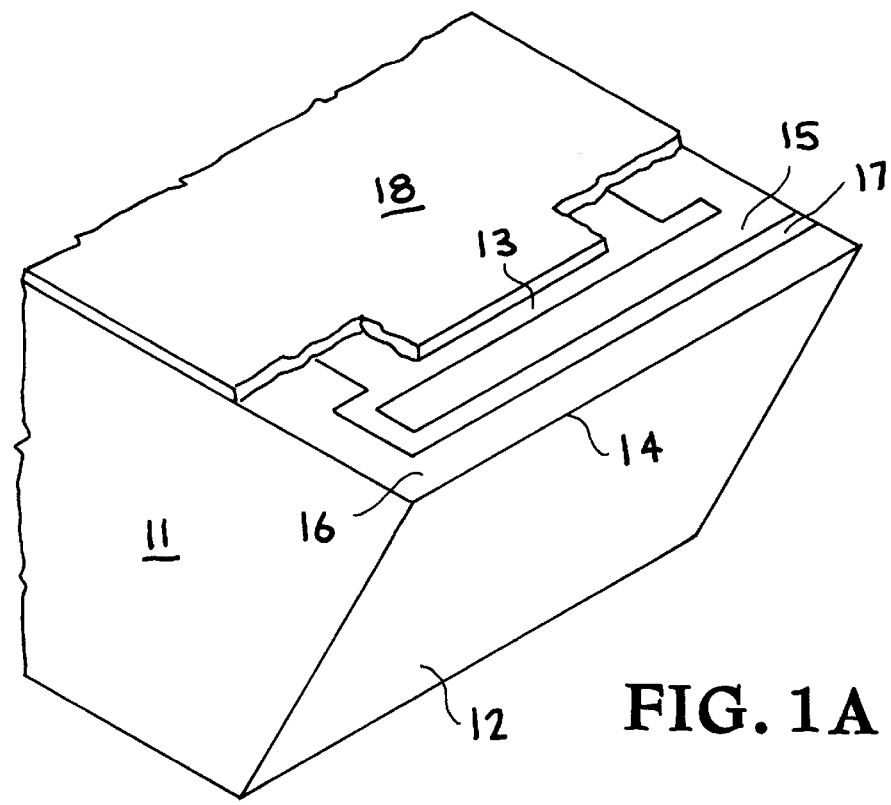
FIG. 1A is an enlarged view of the end of the cauterizer of FIG. 1, illustrating the electrode arrangement.
Figure 2:
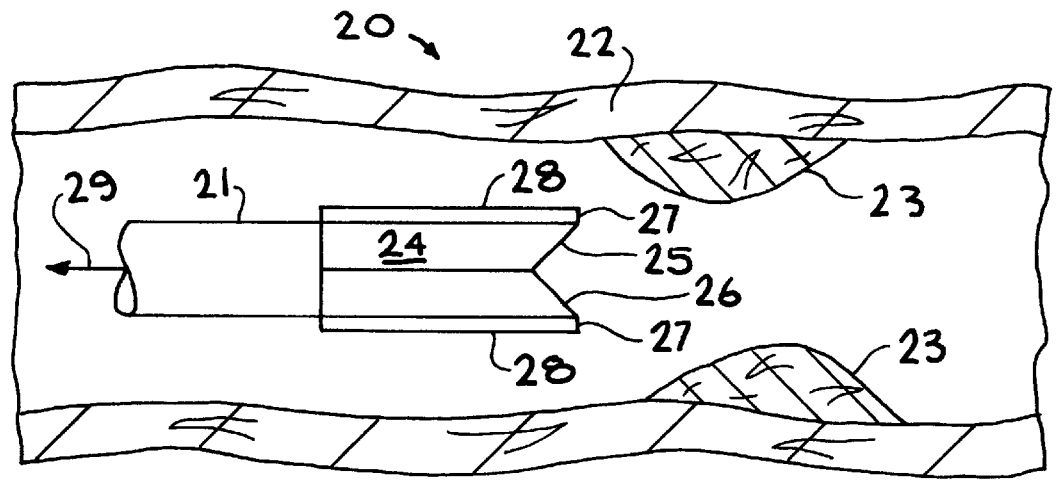
FIG. 2 schematically illustrates another embodiment of a microfabricated electro cauterizer secured to a catheter for suction of tissue removed by knife edges of the cauterizer.

FIG. 2 schematically illustrates another embodiment of an instrument, made in accordance with the invention, inserted into a blood vessel for clot or plaque removal. The microelectro cauterizer instrument of FIG. 2, generally indicated at 20 is attached to a catheter 21 located in a blood vessel 22 having clots or plaque 23 therein. The instrument 20 has a body or member 24 (composed of silicon, glass, ceramics or metal) composed of two bonded sections and having a pair of tapered surfaces 25–26, each terminating in a knife edge 27, and located adjacent knife edges 27 are parallel electrode arrangements generally indicated at 28, each constructed similar to that of FIGS. 1 and 1A. While not shown, in FIG. 2, but clearly illustrated in FIG. 3, the body 24 is provided with a hollow channel whereby tissue cut by knife edges 27 is removed or, flushed out, by suction via the catheter and hollow channel, as indicated by 29.

Figure 3:
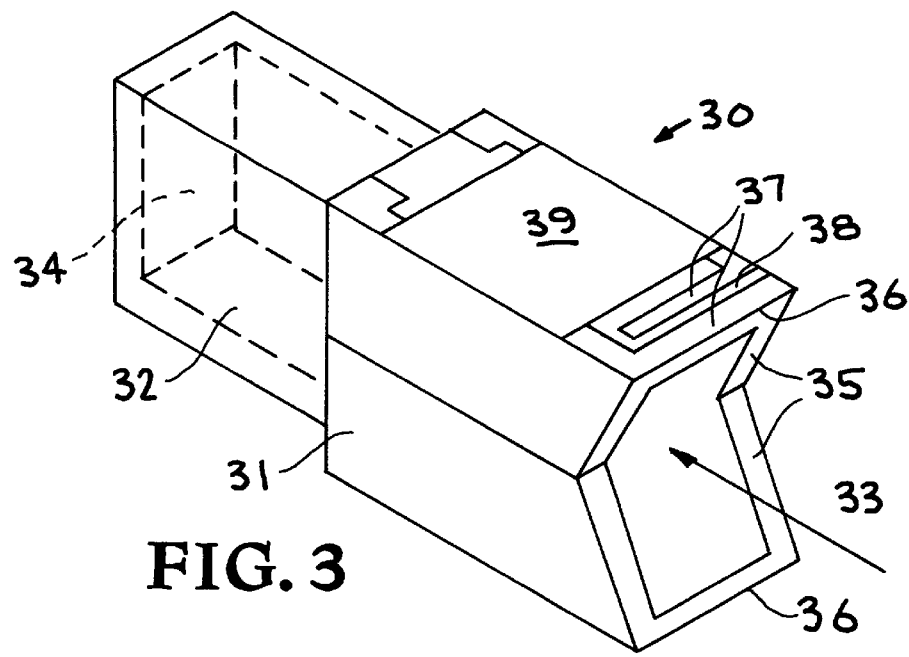
FIG. 3 is a three-dimensional view of an embodiment of a biopsy/cauterizer instrument, similar to that of FIG. 2, and illustrating the hollow channel through which irrigation and/or suction can be carried out.

FIG. 3 illustrates an instrument generally similar to that of FIG. 2, and this embodiment of the microelectro cauterizer, generally indicated at 30 comprises a rectangular shaped body or member section 31 composed of two bonded members and a rectangular shaped adapter or connector section 32 for attachment to a catheter, for example. The body section 31 and adapter section 32 are provided with hollow channels 33 and 34, through which tissue samples maybe withdrawn by suction. Body section 31 includes a pair of tapered surfaces 35 at one end which terminate in knife edges 36. The opposite outer surfaces of the body section 31 are provided with a parallel electrode arrangement 37 defining a bipolar gap 38 located between parallel electrodes, as in FIGS. 1–1A, and having an insulator film or layer 39 constructed as described above with respect to FIGS. 1 and 1A.

By way of example the body section 31, constructed of silicon, may have a length of 0.5 mm to 3 mm, width of 100 $\mu$m to 0.5 mm and height of 200 $\mu$m to 1 mm, with hollow channel 33 defining an inlet of 200 $\mu$m×400$\mu$m. The adapter section 32, constructed of silicon, may have a length of 200 $\mu$m to 2 mm, width of 100 $\mu$m to 1.5 mm, and height of 200

μm to 1 mm, with hollow channel 34 defining an inlet of 200 μm×400 μm. The tapered end surfaces 35 may taper at an angle of 70° to 75°. The body section 31 as shown comprises two halves bonded together, such as by Au/SI eutectic bonding, and are so constructed for ease of fabrication of the tapered end surfaces 35, but may be machined from a single silicon block. While the FIG. 3 embodiment is illustrated as being of a rectangular configuration, it may also be of a square or circular configuration. If of a circular configuration the forward or leading edge of the body could include either tapered sections or an annular taper to form a plurality of curved knife edges or an annular knife edge, and with a plurality or one parallel electrode arrangement. If a square configuration, each of the leading end surfaces could be tapered to defined four knife edges, and each side have a cauterizing electrode arrangement. Either configuration may be particularly beneficial in the removal of plaque from a blood vessel, for example.

Figure 4:
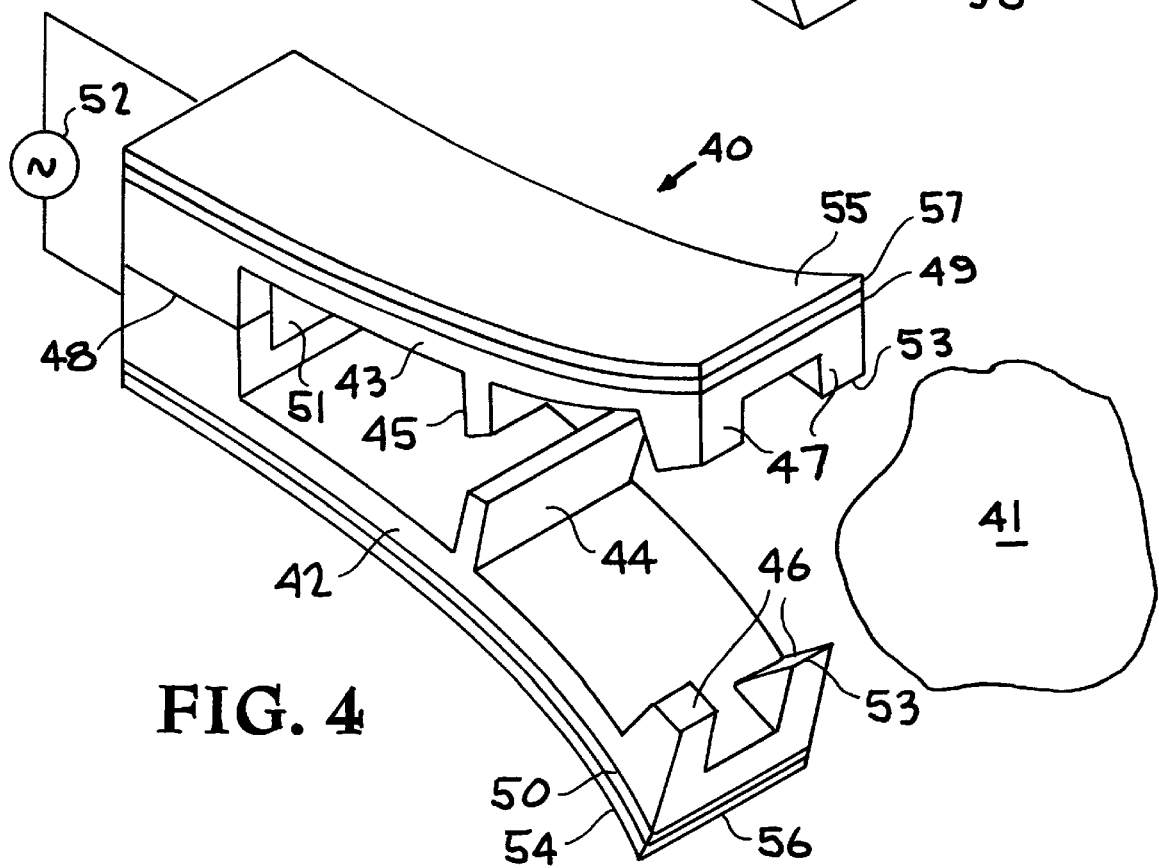
FIG. 4 illustrates a SMA microgripper incorporating biopsy knife edges on the gripper jaws and cauterizing electrodes and provided with a hollow channel for supplying medication to be deposited or to enable irrigation and/or suction when secured to an appropriate catheter.

FIG. 4 illustrates a silicon microgripper instrument, such as disclosed in above-referenced copending application Ser. No. 08/446,146, modified in accordance with the present invention to incorporate electrical cauterizer and biopsy capabilities, as well as drug dispensing and irrigation and/or suction capabilities. The microgripper instrument generally indicated at 40 is adapted, for example, to biopsy and/or cauterize a sample or specimen from a tissue 41. The silicon microgripper instrument 40 utilizes a shape-memory alloy (SMA) thin film actuator and can be locally actuated at low temperatures (<100° C.), with a large gripping force (10 to 40 mN), and has a relatively rigid structural body, and flexibility in functional design. The actuation of the microgripper 40 is generated for example, by one or two SMA films, composed of NiTiCu and can deflect each side of the microgripper up to 55 μm for a total gripping motion of 110 μm. This opening motion corresponds to a 20 mN opening force on the tip of the gripper. The opening jaws, pusher pads, and hollow channel are shaped by a combination of precision sawing and bulk machining of silicon. Two preprocessed silicon wafers or members are precision aligned and selectively bonded, using an Au—Si eutectic process which involves aligning a mask on a wafer and evaporating through the mask onto the gripper bonding portion, as described in greater details in above-referenced application Ser. No. 08/446,146. The microgripper instrument 40 of FIG. 4, may, for example, be 1 mm×200 μm×380 μm in dimensions, having a pair of silicon cantilevers 12.5 μm thick, with 5 μm thick NiTiCu SMA thin films deposited on the outer sides of the cantilevers or gripper arms to provide actuation of the instrument. The SMA thin film can generate actuation stresses up to 500 MPa at transformation temperatures between 30° C. to 70° C.

As shown in FIG. 4, the microgripper instrument 40 includes a pair of silicon cantilevers or gripper members 42 and 43, each having a 30 μm wide pusher pad 44 and 45, respectively, and a pair of 60×110×110×100 μm gripping jaws 46 and 47. The cantilevers are adapted to releasably retain material therein. The gripper members 42 and 43 are Au—Si eutectic bonded at the interface 48, and each is provided with an SMA thin film 49 and 50 on the outer surfaces or sides. The cantilevers or gripper members 42 and 43 are constructed to define a 110 μm wide hollow channel 51 in the area of the bonded interface 48, which is in communication with one end of a catheter, for example, on which the instrument 40 is mounted. The SMA thin films 49 and 50 are connected to a power supply generally indicated at 52 with a control switch means, not shown. The ends of the gripping jaws, 46 and 47 may be flat or etched to define a sharp cutting edge 53 shown on two jaws.

By way of example, the pusher pads 44 and 45 may have a thickness of 20–40 μm and height of 80–100 μm, with the gripping jaws 46 and 47 having a height of 80–100 μm, and a flat end cross-section of 70×150 μm, shown on one set, or an atomically sharp edge 53 shown on another set. The hollow channel 51 has a width of 100–250 μm and height of 50–180 μm. While one set of opposing gripper jaws 46–47 has been shown flat and one set with knife edges both of the gripping jaws 46 may be flat or knife edged and both the gripping jaws 47 may be knife edged or flat, depending on the desired cutting and/or medicine depositing application. While both sets of opposite gripping jaws may be knife edged or one of each set flat edged for biopsy applications if both sets have the knife edges such may puncture containers, for example used for depositing drugs or other material by the cantilevers or gripper members 42 and 43.

The FIG. 4 microgripper instrument 40 additionally includes a pair of cauterizing parallel electrode arrangements 54 and 55 which are formed on the SMA films 49 and 50 with insulation layers 56 and 57 there between. The electrode arrangements are similar to that illustrated in FIGS. 1 and 1A, include an insulation layer, not shown, such as layer 18 in FIGS. 1–1A, and may also be connected to power supply 52 with appropriate control switch or activator not shown. Thus, the FIG. 4 embodiment enables multifunctional operations with a single instrument, which includes cauterization, tissue sampling, drug or medicine depositing, irrigating and/or suction; as well as utilizing the electrode arrangements for biosensor applications.

Figure 5:
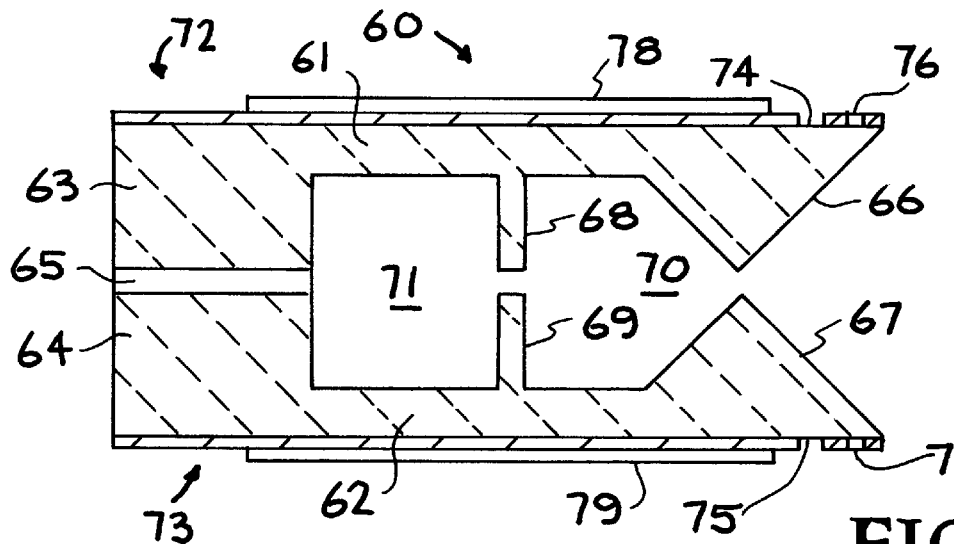
FIGS. 5 and 6 illustrate in cross-section additional embodiments of a cauterizer instrument made in accordance with the present invention.
Figure 6:
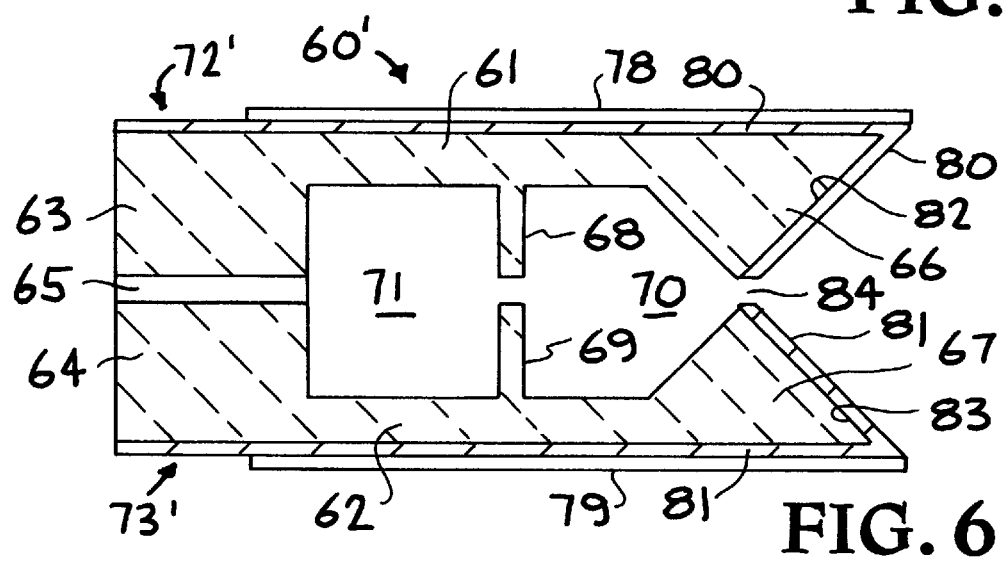

FIGS. 5 and 6 illustrate in cross-section embodiments which are generally similar to the FIG. 3 embodiment and incorporate in the FIG. 5 embodiment an electrode/bipolar gap arrangement similar to that shown in FIGS. 1–1A, while the FIG. 6 embodiment is constructed such that the bipolar gap is formed intermediate cantilever members. Similar components in the embodiments of FIGS. 5 and 6 will be given corresponding reference numerals.

The microgripper instrument illustrated in FIG. 5 is generally indicated at 60 and comprises a pair of cantilevers or members 61 and 62 having respective ends 63 and 64 constructed as in FIGS. 3 and 5 to form an opening 65, with ends 63 and 64 being bonded together, as in FIG. 4. The cantilevers 61 and 62 are constructed to include outer pointed sections 66 and 67 and inner radially extending sections 68 and 69 forming a pusher pad as in FIG. 4, with a gap or cavity 70 formed intermediate sections 66–67 and 68–69, and a gap or cavity 71 formed intermediate sections 68–69 and ends 63–64, with cavity 71 being in open communication with opening 65 in ends 63–64. The cantilevers 61 and 62 are each provided with an electrode arrangement generally indicated at 72 and 73 on outer surfaces 74 and 75 thereof, and which form bipolar gaps 76 and 77, with an insulator layer 78 and 79 formed on each of the electrode arrangements 72 and 73, as illustrated in FIGS. 1–1A. While not shown, the cantilevers 61 and 62 may inlcude layers or films of SMA material, as in FIG. 4, or a balloon located in cavity 70 or 71, to move the cantilevers relative to each other, or move one cantilever relative to the other. Thus, the outer pointed cantilever sections 66 and 67 may be utilized for tissue sampling or drug deposition, etc. as described above, while the radially extending sections 68–69 may be utilized to transport drugs, etc. to a point of use, while the electrode arrangement may be utilized to cauterize a tissue area or for biosensor applications, as described above.

The FIG. 6 embodiment differs from FIG. 5 by the use of a single bipolar gap located intermediate pointed end sections of the cantilevers, and thus utilizes a single electrode on each of the cantilevers. As shown, the instrument of FIG. 6 generally indicated at 60' is constructed as described above with respect to FIG. 5, except that the electrode arrangements generally indicated at 72' and 73' are composed of a single electrode 80 and 81 on each cantilever, and additionally are formed on outer surfaces 82 and 83 of pointed sections 66 and 67 of cantilevers or members 61 and 62, whereby a bipolar gap 84 is formed therebetween.

It has thus been shown that the present invention provides a micromachined electric cauterizer which can be utilized alone, in combination with tissue sampling and/or irrigation and/or suction and/or medication depositing. In addition the electrodes of the cauterizer can also be used as sensing devices to probe the electrical resistance of areas of tissue, etc., to discriminate, for example, between clots and tissue. The instrument embodiments of this invention can improve precision microsurgery by reducing costs and increasing efficiency, as well as enabling microsurgery to be more accurate with more controls in small manipulation areas. The MEMS technique enables the provision of miniature sizes, multiple functionality, sharper incisions, and closely-spaced electrodes for point cauterization, and can be effectively used through intravascular catheters to reach formerly unreachable areas of the human anatomy. The economic benefits are high not only because of the inventions potential in minimally invasive therapeutic procedures (which typically reduce hospitalization time), and which are less traumatic to the patient, but also because of the lithographic processes of microfabrication which renders batch production of the instruments. In addition, by focusing the energy at a micro scale, the efficiency is enhanced and therefore the power required to cut and/or cauterize is greatly reduced.

While specific embodiments, materials, parameters, etc. have been set forth to exemplify and explain the principles of the invention, such are not intended to be limiting. Modifications and changes may become apparent to those skilled in the art, and it is intended that the invention be limited only by the scope of the appended claims.

The invention claimed is:

1. A micromachined electrical cauterizer, comprising:
    a body member constructed of silicon having at least one tapered surface defining at least one knife edge adapted for sampling tissue, and
    a pair of microelectrodes formed on said body member for producing localized electro cauterization,
    said microelectrodes forming a bypolar gap adjacent one end of said body member.
2. The cauterizer of claim 1, wherein said body member includes a hollow channel therein.
3. The cauterizer of claim 1, wherein said tapered surface of said body member is located at an end thereof terminating in a knife edge for cutting tissue.
4. The cauterizer of claim 1, wherein said microelectrodes are formed on opposite sides of said body member, and wherein said body member has end sections defining at least two tapering surfaces having knife edges at outer ends thereof.
5. The cauterizer of claim 4, wherein said body member additionally includes a hollow channel extending from said tapering surfaces.
6. The cauterizer of claim 5, in combination with a catheter, said catheter being connected to one end of said body member.
7. The cauterizer of claim 1, wherein said body member includes a pair of cantilevered sections, each of said cantilevered sections having at least one of said microelectrodes formed thereon.
8. The cauterizer of claim 7, additionally including means for moving at least one of said cantilevered sections.
9. The cauterizer of claim 8, wherein said means for moving said at least one of said cantilevered sections comprises a shape-memory alloy film located on at least one of said cantilevered sections.
10. The cauterizer of claim 7, wherein said body member additionally includes a hollow channel extending therethrough.
11. The cauterizer of claim 7, wherein said pair of cantilevered sections, each include at least one gripper member at the outer edge thereof.
12. The cauterizer of claim 11, wherein at least one of said gripper members includes a tapered surface forming a knife edge.
13. The cauterizer of claim 7, wherein at least one of said cantilevered sections is provided with a pusher pad.
14. The cauterizer of claim 1, wherein said body member is composed of two sections bonded together.
15. The cauterizer of claim 1, wherein said body member includes a pair of cantilevers, and wherein said microelectrodes are located on each of said cantilevers.
16. The cauterizer of claim 15, wherein said microelectrodes are composed of an electrode on each of said cantilevers, and wherein said bipolar gap is formed between said cantilevers.
17. A micromachined instrument having a body member constructed of silicon and having multi-functions and adapted to operate in a fluid vessel comprising:
    means for sampling tissue including a surface having a knife edge formed thereon,
    means for cauterizing an area of the sampled tissue including microelectrodes formed on said body member to define a bipolar gap, and
    means by which sampled tissue can be removed.
18. The instrument of claim 17, additionally including means for releasably retaining material, and wherein said means by which sampled tissue can be removed additionally enables irrigation of a tissue area.
19. The instrument of claim 18, wherein said means for releasably retaining material includes a member having movable cantilevers with gripping means at an outer end of at least one of said movable cantilevers, and wherein said means for removing sampled tissue and for irrigation of a tissue area includes a hollow channel formed in said member.
20. The instrument of claim 17, additionally including means for tissue sensing of electrical resistance to discriminate between healthy tissue and clots/plaque.
21. The instrument of claim 17, wherein said means for sampling tissue includes a pair of cantilevers, and wherein each of said cantilevers include a microelectrode constructed to define a bipolar gap intermediate ends of said pair of cantilevers.
22. The instrument of claim 21, wherein said end of said pair of cantilevers include pointed sections, and wherein said microelectrodes extend along surfaces of said pointed sections of said cantilevers.

* * * * *